United States Patent [19]

Ogle

[11] 3,945,382

[45] Mar. 23, 1976

[54] DEVICE FOR INTRODUCTION OF LIQUID MEDICATION INTO A FLEXIBLE BAG

[75] Inventor: Robert Walter Ogle, Newport Beach, Calif.

[73] Assignee: IMS Limited, S. El Monte, Calif.

[22] Filed: Apr. 15, 1974

[21] Appl. No.: 461,066

Related U.S. Application Data

[62] Division of Ser. No. 314,705, Dec. 13, 1972, Pat. No. 3,828,779.

[52] U.S. Cl................................... 128/272; 128/220
[51] Int. Cl.²............................................ A61J 1/00
[58] Field of Search ........ 128/221, 272, 215, 214.2, 128/214 C, 214 F, 214 D, 218 D, 218 N, 216, 218 M, 220

[56] References Cited
UNITED STATES PATENTS

| | | | |
|---|---|---|---|
| 2,724,383 | 11/1955 | Lockhart......................... | 128/272 X |
| 2,904,043 | 9/1959 | Friedman........................ | 128/218 D |
| 3,123,072 | 3/1964 | Bellamy, Jr..................... | 128/221 |
| 3,336,924 | 8/1967 | Sarnoff et al................... | 128/218 M |
| 3,376,866 | 4/1968 | Ogle................................ | 128/272 X |
| 3,416,528 | 12/1968 | Kahn............................... | 128/214.2 |
| 3,542,023 | 11/1970 | Ogle................................ | 128/218 M |
| 3,659,602 | 5/1972 | Cloyd.............................. | 128/220 |

FOREIGN PATENTS OR APPLICATIONS

| | | | |
|---|---|---|---|
| 1,441,924 | 3/1969 | Germany........................ | 128/272 |
| 686,219 | 5/1964 | Canada........................... | 128/272 |
| 751,433 | 6/1933 | France............................ | 128/221 |

*Primary Examiner*—John D. Yasko
*Attorney, Agent, or Firm*—Wills, Green & Mueth

[57] ABSTRACT

A device for the introduction of liquid medication into a flexible bag for the administration of intravenous solutions. The device comprises an elongated generally cylindrical hollow tubular member having an open end and a closed end, a boss extending from the closed end carried by the boss a cannula having a sharpened outer end, and a rigid sheath surrounding the cannula and carried by the boss. The sheath serves to limit the advancement of the cannula into an orifice having a diameter greater than that of said cannula. A thrust portion is provided within the tubular member and a fluid passage extends longitudinally through the center of the thrust portion. The lower end of the fluid passage communicates with the upper end of the cannula. A cylindrical vial having a resilient stopper in its open end seals on the inside walls of the vial. There are threads on the thrust portion and cooperating threads on the stopper adapted to be interlocked, whereby the plug can be interlocked with the thrust portion.

2 Claims, 7 Drawing Figures

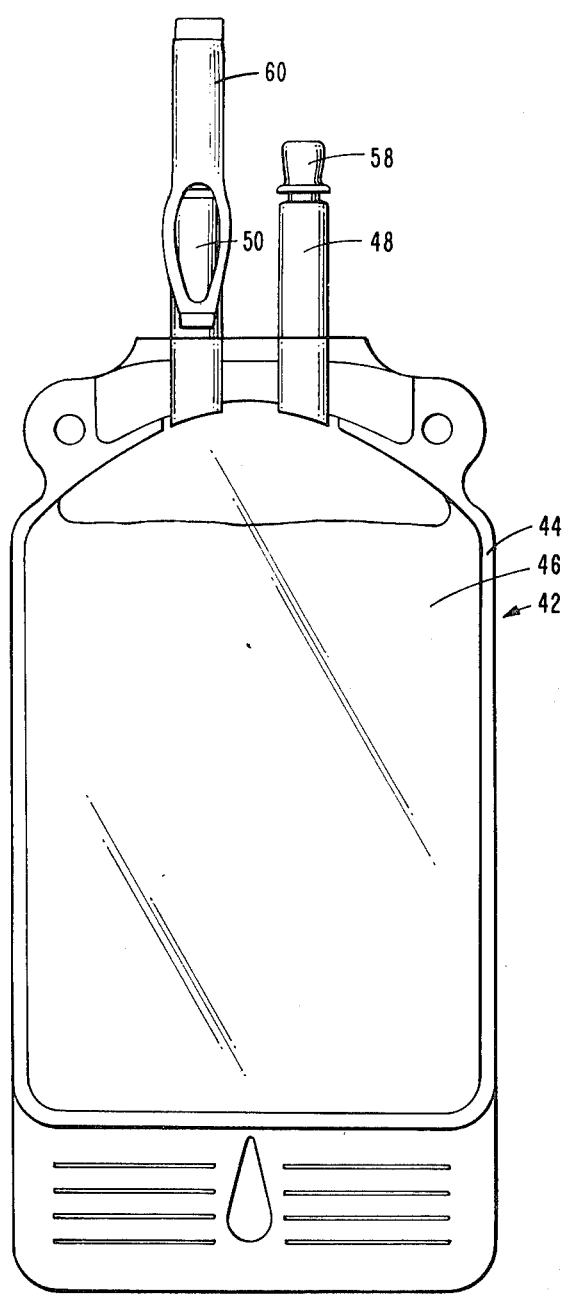
FIG.—1
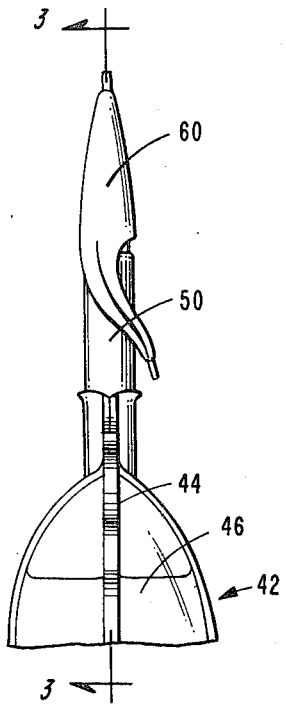
FIG.—2

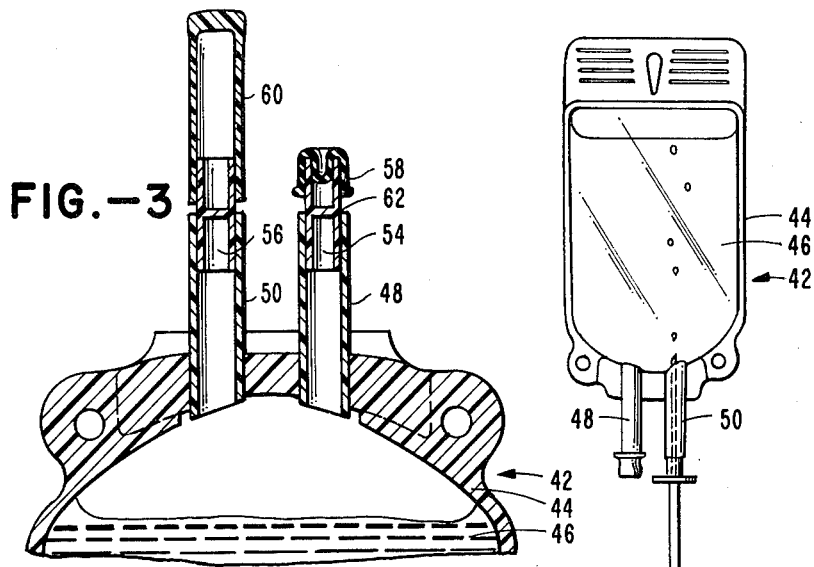
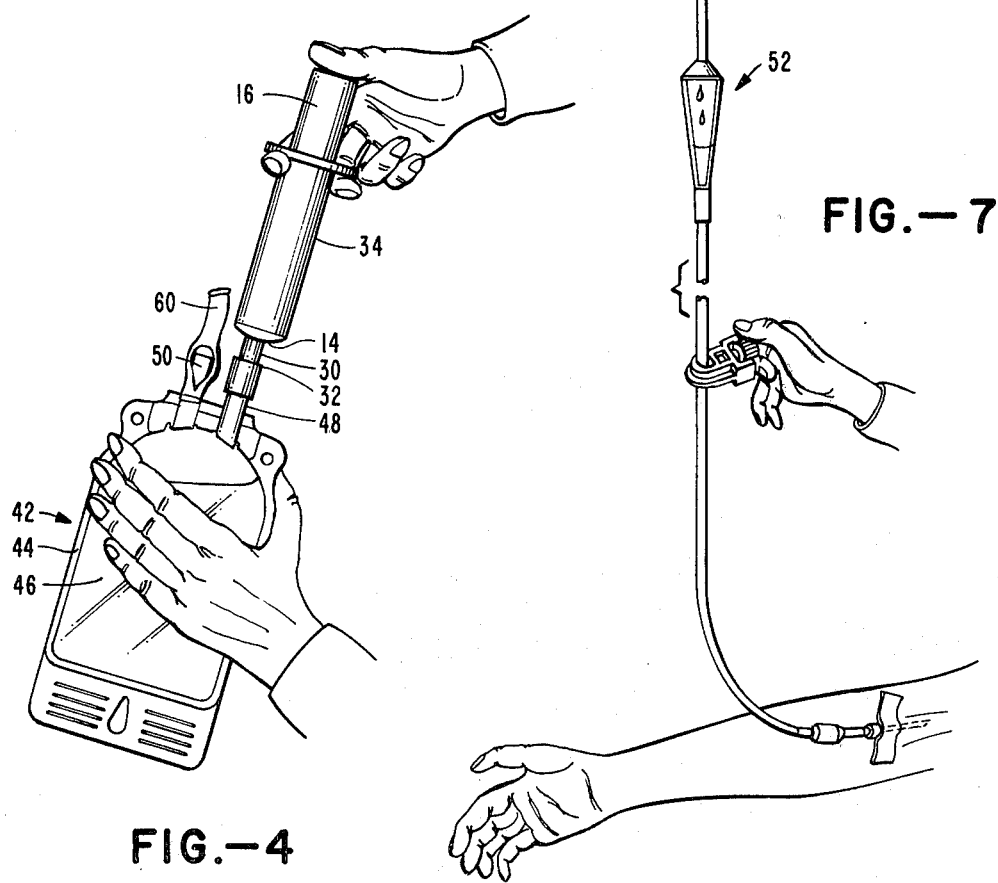

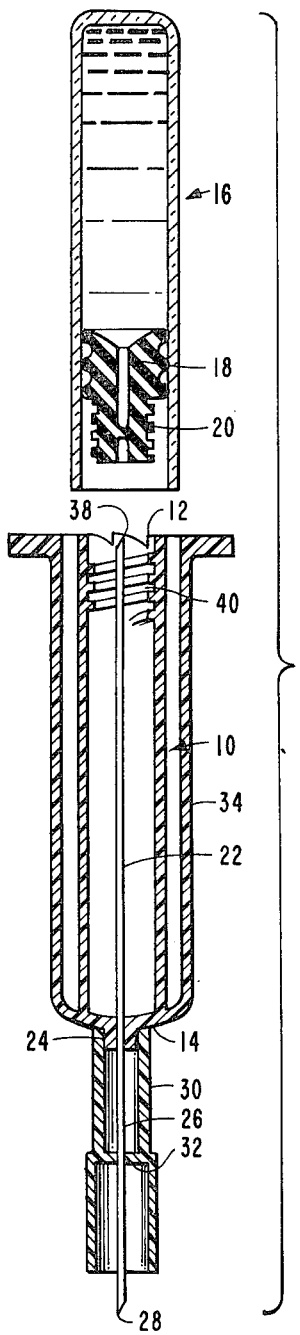
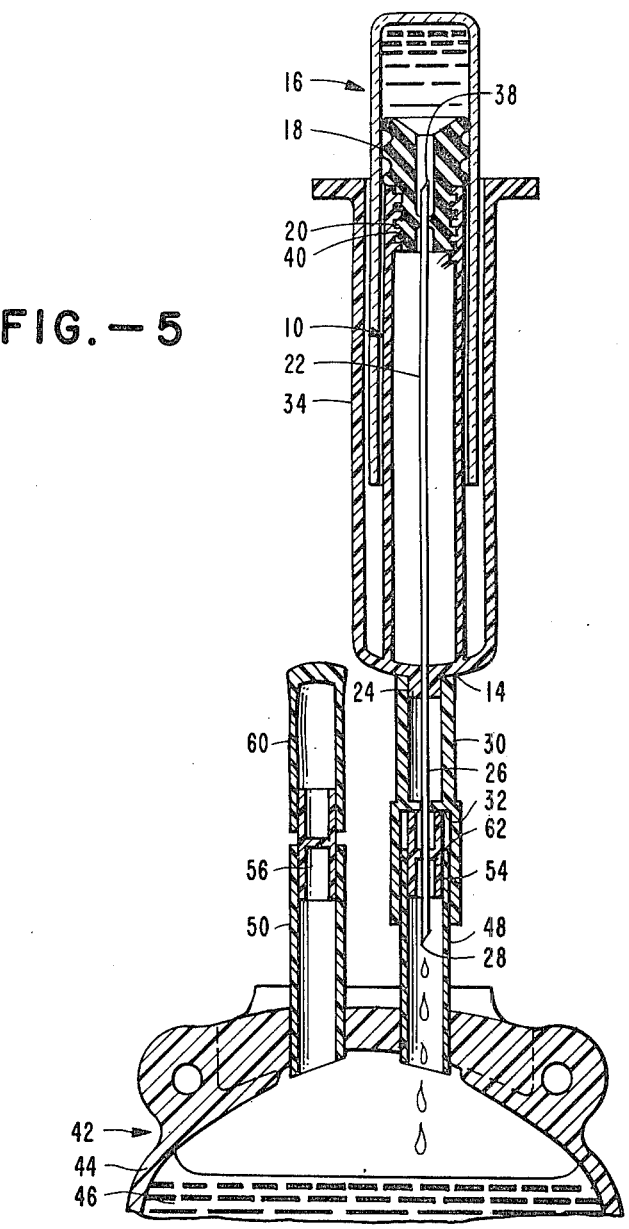

3,945,382

DEVICE FOR INTRODUCTION OF LIQUID MEDICATION INTO A FLEXIBLE BAG

BACKGROUND OF THE INVENTION

This application is a division of Ser. No. 314,705, filed Dec. 13, 1972, now U.S. Pat. No. 3,828,779, the disclosure of which is incorporated herein by reference.

The present invention is concerned with a device which is useful for the addition of medicinal solutions to flexible intravenous solution bags. Various devices have been proposed for these purposes. In general, the devices involve the use of metal conventional syringes. The problems are several. First, medication for addition to intravenous solution bags is frequently of high concentration, much too high for direct injection into the patient. Thus, the packaging of concentrated medication in a syringe presents the hazard of mistaken use, viz, direct injection rather than dilution by addition to the intravenous solution. Secondly, the orifice or inlet on the typical intravenous solution bag is flexible as is the bag itself. The insertion of an ordinary syringe into the orifice tube can result in the puncturing of the orifice tube and/or bag unless great care is observed. The present invention effectively overcomes these problems in the art.

SUMMARY OF THE INVENTION

Briefly, the present invention comprises a device for the introduction of liquid medication into a flexible bag for the administration of intravenous solutions which comprises an elongated generally cylindrical hollow tubular member having an open end and a closed end, a boss extending from said closed end, carried by the boss a cannula having a sharpened outer end, a rigid sheath surrounding said cannula and carried by said boss, said sheath serving to limit the advancement of the cannula into an orifice having a diameter greater than that of said cannula; within said tubular member a thrust portion within said tubular member, a fluid passage extending longitudinally through the center of said thrust portion, the lower end of said fluid passage communicating with the upper end of said cannula, a cylindrical vial having a resilient stopper in its open end sealing on the inside walls of said vial, interlocking means on said thrust portion and cooperating interlocking means on said stopper, whereby upon interlocking of said plug with said thrust portion said vial is first held in an assembled but non-operating position and upon further interlocking of said plug with said cylindrical member, said plug is adapted to be pierced by said fluid passage and said fluid passage with said vial without the application of substantial axial pressure on said plug and said plug is locked securely to said cylindrical member to permit aspiration upon withdrawal of said vial or to permit expulsion of the contents of said vial upon exertion of pressure on said vial.

This invention also includes the combination of a flexible bag for intravenous solution having an additive-receiving orifice and an outlet adapted to lead to an intravenous solution set, and a device for the introduction of liquid medication into said flexible bag comprising an elongated generally cylindrical hollow tubular member having an open end and a closed end, a boss extending from said closed end, carried by the boss a cannula having a sharpened outer end, a rigid sheath surrounding said cannula and carried by said boss, said orifice having a diameter greater than that of said cannula, said sharpened outer end being received in said orifice and said sheath engaging said orifice to limit the advancement of said cannula into the orifice; within said tubular member, a thrust portion within said tubular member, a fluid passage extending longitudinally through the center of said thrust portion, the lower end of said fluid passage communicating with the upper end of said cannula, a cylindrical vial having a resilient stopper in its open end sealing on the inside walls of said vial, interlocking means on said thrust portion and cooperating interlocking means on said stopper, whereby upon interlocking of said plug with said thrust portion said vial is first held in an assembled but non-operating position and upon further interlocking of said plug with said cylindrical member, said plug is adapted to be pierced by said fluid passage and said fluid passage communicated with said vial without the application of substantial axial pressure on said plug and said plug is locked securely to said cylindrical member to permit aspiration upon withdrawal of said vial or to permit expulsion of the contents of said vial upon exertion of pressure on said vial.

It is an object of the present invention to provide a novel device for the packaging of medication.

More particularly, it is an object of the present invention to provide for the packaging of medication in a disposable device.

Still another object of the present invention is to provide a disposable device for use in the addition of medication to intravenous solution bags.

These and other objects and advantages of the invention will be apparent from the more detailed description which follows taken in conjunction with the accompanying drawings.

Further, the device of the present invention includes a significant safety feature. Additives for intravenous solutions actually contain medication in a concentration unsuitable for direct injection into the human body. In fact, many of these additives are fatal if directly injected. The sheath on the device of this invention prevents the accidental injection of the concentrated medication into the body. The sharpened cannula end of this invention also prevents coring of the rubber diaphragm on the intravenous solution bag. Coring results in bits of rubber falling into the solution which can result in the injection of this dangerous blood clotting material into the patient.

DESCRIPTION OF THE PREFERRED EMBODIMENTS

Turning to the drawings:

FIG. 1 shows a perspective view of a conventional intravenous solution bag.

FIG. 2 is a partial side view of the bag in FIG. 1.

FIG. 3 is a sectional view of the upper portion of the bag of FIG. 1 taken along the line 3—3 in FIG. 2.

FIG. 4 shows, in assembled form, the bag of FIG. 1 in relationship to the novel syringe having a sheath.

FIG. 5 shows a sectional view of the novel syringe of the present invention in disassembled form.

FIG. 6 is an enlarged partial sectional view of the combination shown in FIG. 4.

FIG. 7 shows, in assembled form, the use of the intravenous administration bag after the addition of FIG. 4 has been completed.

Turning to the drawings in greater detail, the holder of FIGS. 4–6 comprises a generally cylindrical hollow thrust portion 10 having an open end 12 and a closed end 14. The cylindrical vial 16 has a resilient stopper 18 in its open end sealing on the inside walls of the vial 16. The stopper 18 generally, although not necessarily, has a thin imperforate central diaphragm portion. The stopper 18 is provided with an externally threaded projection 20 thereon. The thrust portion 10 has a needle 22 therein and a boss 24 on its exterior from which cannula 26 extends. The cannula 26 has a sharpened outer end 28. The sheath 30 is carried by boss 24 and surrounds cannula 26. The sheath 30 terminates short of the sharpened outer end 28 of cannula 26. The sheath 30 has an offset or shoulder 32 which functions as further hereinafter described. Thrust portion 10 may be surrounded by holder 34.

The upper end of needle 22 has a sharp terminal portion 38. The thrust portion 10 may have internal threads 40 in proximity to its upper end, the threads on the projection 20 and the threads 40 being adapted when made up to cause said sharp terminal portion 38 of the needle 22 to puncture said stopper 18. When the projection 20 is made up with threads 40, the stopper 18 functions as a piston to expel the contents of the vial 16 through needle 22 as said vial 16 is advanced with respect to said thrust portion 10.

The flexible intravenous solution bag 42 usually has a heat-sealed peripheral portion 44 and a solution-containing zone 46. The bag also has a flexible orifice or inlet tube 48 and an outlet tube 50 which leads to a conventional intravenous solution administration set 52. The inlet tube and outlet tubes are provided with imperforate diaphragms 54 and 56, respectively, and removable caps or closures 58 and 60, respectively.

In operation, caps 58 and 60 are removed, the cannula 26 and sheath 30 are positioned as shown in FIG. 6, that is, the offset or shoulder 32 limits the advancement of cannula into tube 48 so that the sharpened end 28 of cannula 26 pierces diaphragm 54 but the inside of shoulder 32 engages the outer end 62 of tube 48, limiting the advancement of the cannula 26 within tube 48. The flat surface of the shoulder 32 also serves to maintain the cannula 26 in a parallel or longitudinal relationship with respect to the inside walls of tube 48, thereby reducing the possibility of the sharpened end 28 piercing the side of tube 48. By limiting the advancement of the cannula 26 in tube 48 there is no chance that the sharpened end 28 can pierce the solution-containing zone 46. Thus, the escape of solution and the introduction of contaminated hospital air into the system are prevented.

With the parts as shown in FIG. 4, the vial is normally first withdrawn slightly to aspirate from the bag into the vial approximately that volume of air corresponding to the volume of additive medication in the vial. Then, the contents of the vial are expressed into the bag. The purpose of such aspiration is to prevent rupture of the bag due to over-pressurization.

As will be understood by those skilled in the art, once the contents of vial 16 have been transferred to zone 46, the bag 42 is then hung up as shown and connected to the patient via set 52, as shown in FIG. 7.

Having fully described the invention it is intended that it be limited only by the lawful scope of the appended claims.

I claim:

1. A device for the introduction of liquid medication into a flexible bag for intravenous solution, said bag having extending from the top thereof an additive-receiving flexible tube-like orifice and an outlet adapted to lead to an intravenous solution set, said device comprising an elongated generally cylindrical hollow tubular member having an open end and a closed end, a boss extending from said closed end, carried by the boss a cannula having a sharpened outer end, a rigid cylindrical sheath of fixed length surrounding said cannula and affixed to said boss, said sharpened outer end extending slightly beyond the free end of said sheath, said orifice having a diameter greater than that of said cannula, said sharpened outer end being adapted to be received in said flexible tube-like orifice and said sheath being adapted to engage said orifice to limit the advancement of said cannula into the orifice; within said tubular member, a thrust portion, a fluid passage extending longitudinally through the center of said thrust portion, the lower end of said fluid passage communicating with the upper end of said cannula at said boss, a cylindrical vial having a resilient stopper in its open end sealing on the inside walls of said vial, interlocking means on said thrust portion and cooperating interlocking means on said stopper, whereby upon interlocking of said plug with said thrust portion said vial is first held in an assembled but non-operating position and upon further interlocking of said plug with said cylindrical member, said plug is adapted to be pierced by said fluid passage and said fluid passage communicated with said vial without the application of substantial axial pressure on said plug and said plug is locked securely to said cylindrical member to permit aspiration upon withdrawal of said vial or to permit expulsion of the contents of said vial upon exertion of pressure on said vial.

2. The device of claim 1 wherein the sheath has two portions of different diameter, the outer portion having a diameter greater than the outside diameter of said orifice and the inner portion having a diameter less than the outside diameter of said orifice whereby an annular shoulder is provided at the junction of said portion which is adapted to abut the outer end of said orifice.

* * * * *